(12) United States Patent
van Dijk et al.

(10) Patent No.: US 10,098,328 B2
(45) Date of Patent: Oct. 16, 2018

(54) METHOD OF MONITORING THE PHYSICAL CONDITION AND/OR SUITABILITY OF ANIMAL FEED OF RUMINANT ANIMALS

(71) Applicant: N.V. Nederlandsche Apparatenfabriek NEDAP, Groenlo (NL)

(72) Inventors: Jeroen Martin van Dijk, Groenlo (NL); Rudie Jan Hendrik Lammers, Groenlo (NL); Jan Anne Kuipers, Groenlo (NL)

(73) Assignee: N.V. NEDERLANSCHE APPARATENFABRIEK NEDAP, Groenlo (NL)

( * ) Notice: Subject to any disclaimer, the term of this patent is extended or adjusted under 35 U.S.C. 154(b) by 77 days.

(21) Appl. No.: 15/342,603

(22) Filed: Nov. 3, 2016

(65) Prior Publication Data

US 2017/0231199 A1   Aug. 17, 2017

(30) Foreign Application Priority Data

Nov. 5, 2015  (NL) ..................... 2015730

(51) Int. Cl.
| | |
|---|---|
| *G08B 6/00* | (2006.01) |
| *A01K 29/00* | (2006.01) |
| *G06F 19/00* | (2018.01) |
| *A01K 11/00* | (2006.01) |

(52) U.S. Cl.
CPC .......... *A01K 29/005* (2013.01); *A01K 11/006* (2013.01); *G06F 19/00* (2013.01); *G06F 19/3418* (2013.01)

(58) Field of Classification Search
CPC ............................ A01K 29/005; A01K 11/006
USPC ....................................................... 340/573.1
See application file for complete search history.

(56) References Cited

U.S. PATENT DOCUMENTS

| | | | | |
|---|---|---|---|---|
| 5,984,875 A | * | 11/1999 | Brune | A01K 11/007 |
| | | | | 119/174 |
| 6,689,056 B1 | * | 2/2004 | Kilcoyne | A61B 5/0031 |
| | | | | 128/898 |
| 7,026,939 B2 | * | 4/2006 | Letkomiller | A01K 11/006 |
| | | | | 340/572.7 |

(Continued)

FOREIGN PATENT DOCUMENTS

WO   2014/199361 A1   12/2014

OTHER PUBLICATIONS

Dutch Search Report and Written Opinion of the Dutch Searching Authority, dated Jul. 22, 2016 (8 pages).

*Primary Examiner* — Eric M Blount
(74) *Attorney, Agent, or Firm* — Jacobson Holman, PLLC.

(57) ABSTRACT

A method of monitoring the physiological condition, and/or suitability of animal feed, of ruminant animals, comprising:
a. sensing the occurrence of at least a first predetermined type of activity of the animal;
b. determining a length of a time period of a first type during which in step a. a sensed first predetermined type of activity has taken place;
c. transmitting information about the length of a time period of the first type determined in step b. wherein preferably the transmission starts on a moment in time which depends on the moment in time on which the time period of the first type has ended;
d. repeating steps a.-c. for next sensed occurrences of activities of the first predetermined type.

29 Claims, 3 Drawing Sheets

(56) References Cited

U.S. PATENT DOCUMENTS

| | | | |
|---|---|---|---|
| 7,350,481 B2 * | 4/2008 | Bar-Shalom | A01K 29/005 |
| | | | 119/859 |
| 2007/0088194 A1 * | 4/2007 | Tahar | A01K 11/007 |
| | | | 600/102 |
| 2009/0287103 A1 | 11/2009 | Pillai | |
| 2010/0085249 A1 * | 4/2010 | Ferguson | G01S 19/04 |
| | | | 342/357.41 |
| 2012/0099506 A1 * | 4/2012 | Song | H04H 20/57 |
| | | | 370/312 |

\* cited by examiner

FIG. 6

METHOD OF MONITORING THE PHYSICAL CONDITION AND/OR SUITABILITY OF ANIMAL FEED OF RUMINANT ANIMALS

BACKGROUND OF THE INVENTION

The present invention relates to a method of monitoring the physiological condition and/or suitability of animal feed of ruminant animals, comprising:
- a. sensing the occurrence of at least one predetermined type of activity of the animal;
- b. determining information about a time period of the first type which corresponds with the duration of the at least one predetermined type of activity which is detected in step a.;
- c. repeating steps a. and b. for next sensed occurrences of activities of the at least one predetermined type;
- d. transmitting the information determined in steps b.

Such a method is known from U.S. Pat. No. 7,350,481. In the known method the at least one predetermined type of activity is chewing. The chewing action is measured by means of a sound sensor. Use is made of a data processor for accumulating both the time of each of said sensed chewing actions and the number of such chewing actions per unit time interval, for determining the chewing rhythm of the animal indicating rumination activities over a predetermined time period. The information determined by the data processor is subsequently transmitted by means of a transmitter towards a remote receiver.

A disadvantage of the known method is that the content of the transmitted information may be incomplete because data may be lost.

BRIEF SUMMARY OF THE INVENTION

In accordance with a first aspect of the invention, the method as discussed above comprises also the following steps: the information transmitted in step d is in the format of information blocks of a fixed bit length, each information block comprising a first predetermined number of bits indicating which predetermined type of activity has been detected in step a. and a second predetermined number of bits indicating the information about a time period of the first type as determined in step b. and associated with the sensed occurrence in step a. wherein the second predetermined number of bits cover a time period which is smaller than or equal to a predetermined maximum length in time.

Because in accordance with the invention the information about a length of the at least one predetermined type of activity is not transmitted in a format of the duration of the activity per predetermined time period but as information about the length as such, the chance that information gets lost is relatively low. The at least one predetermined type of activity could for example be rumination.

Preferably it holds that in case that a length of a time period of the first type is smaller than or equal to the predetermined maximum length in time than the information of a determined length of a time period of the first type wherein the associated detected at least one predetermined type of activity has taken place is recorded in one information block, wherein in case that a length of a time period of the first type is larger than the predetermined maximum length in time than: the information of a length of a time period of the first type wherein the associated detected at least one predetermined type of activity has taken place is recorded in a plurality of information blocks or the information of a length of a time period of the first type wherein the associated detected at least one predetermined type of activity has taken place is recorded in one extended information block, wherein the extended information block comprises a sufficient number of additional bits to store the information about the length of a time period of the first type.

At the same time information about other types of predetermined of activities may be transmitted as will be discussed hereinafter. Therefore in accordance with a special embodiment according to the invention it holds that, step a. and step b. are also carried out for a plurality of predetermined type of activity respectively. It follows that each information block relates to only one predetermined type of activities respectively and comprises information about the length of this activity which length is however smaller than or equal to a predetermined maximum value due to the fixed maximum number of bits reserved to register. This is true unless the length of an information block is extended based on the desired special embodiment.

The other predetermined type of activity may be one of eating, resting and optionally a rest group of activities. A rest group may for example be activities other than eating, ruminating and resting.

In each of the discussed embodiments it may further hold that in step d. transmission is repeated on random or predetermined moments in time. Possibly in step d. transmission of a predetermined number of the latest determined information blocks is transmitted.

Preferably it holds that the method comprises further a step e. wherein the information transmitted in step d. is received and a step f. wherein, based on the received information in a step e. a time period of the second type associated with the at least one predetermined activity is determined which ends on the moment in time on which the time period of the first type associated with the latest sensed occurrence of the at least one predetermined type of activity has ended and which starts on the moment in time on which the previous time period of the first type, associated with the previous sensed occurrence of the at least one predetermined type of activity has ended.

The method may further comprise a step g. wherein, based on the received information in step f., processed information $Y_f t$ about the length of a time period of the first type associated with the at least one predetermined type of activity is determined as $Y_f t = at.X_f t + (1-at).Y_f t-1$. wherein $X_f t$ is the length of a time period of the first type associated with the latest sensed at least one predetermined type of activity divided by the length of the latest determined time period of the second type associated with the at least one predetermined type of activity wherein $Y_f t-1$ is the processed information about a previous length of a time period of the first type associated with the at least one predetermined type of activity and wherein at is a predetermined factor wherein $0 < at \leq 1$.

Thus it holds that the information $Y_f(t)$ which is determined depends on the length of the time period of the first type as well as the information about a previous length of a time period of the first type. Thereby strong variations in the determined information $Y_f(t)$ are avoided: the information $Y_f t$ also depends on information $Y_f (t-1)$ so that the information $Y_f t$ is in fact filtered information.

Preferably it holds that the information $Y_f(t)$ about the determined length of a time period is respectively determined for the predetermined activities ruminating, eating, resting and optionally an activity relating to a rest group of activities.

It may further hold that at is fixed or at is the length of the latest determined time period of the second type divided by a constant factor C.

It follows from the above that in accordance with the discussed preferred embodiments, the information $Y_f(t)$ about the length of a time period of the first type is not, for example, a time of a rumination action per predetermined time interval. The first difference is that there is no predetermined time interval, the second difference being that the information $Y_f t$ which is determined not only depends on the time of one rumination action but actually also on the length of time of previous rumination actions. The advantage is a filtering effect so that the information which is determined is more suitable for proper interpretation wherein, for example, incorrect determined activities of rumination which are, for example, relatively short are filtered out because the processed information depends on at least two determined rumination actions.

BRIEF DESCRIPTION OF THE DRAWINGS

The invention will now be further discussed based on the drawings, wherein.

Figure 1:
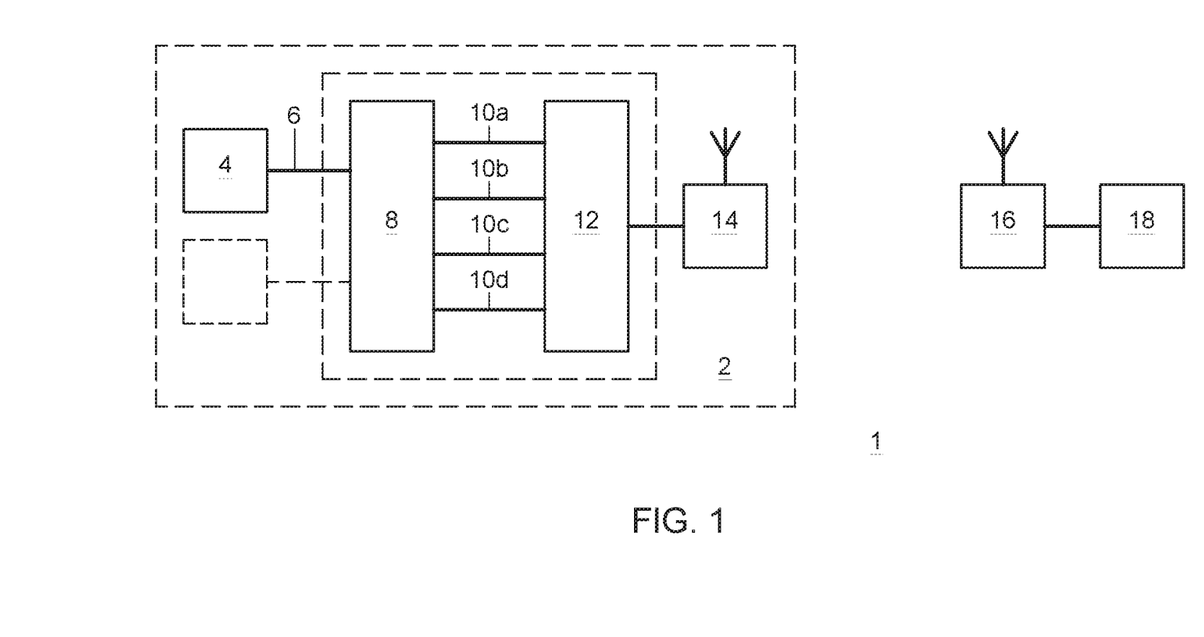
FIG. 1 shows an embodiment of a system in accordance with the invention for carrying out a method according to the invention.

In FIG. 1 reference number 1 indicates a system for monitoring the physiological condition, and/or suitability of an animal feed of ruminant animals.

The system 1 is provided with a device 2 which, in use, can be attached to the animal, for example to the animal's neck. Thus the device may take the form of a well-known tag which can be attached to the animal. The device 2 is provided with at least one sensor 4. In this example the sensor 4 is a so-called 3G sensor which may sense the acceleration and/or direction of the 3G sensor 4. The information generated by the sensor 4 is submitted to a second processing means 8 via a lead 6.

The second processing means 8 is arranged to analyze the signals generated by the sensor 4 for determining whether the animal performs at least one predetermined type of activity. In this example one of the predetermined type of activities is rumination. If the predetermined type of activity ruminating occurs, the second processing means generates a signal indicating rumination on lead 10a. The second processing means 8 are also arranged to sense the occurrence of other predetermined types of activities based on the signals generated by the sensor 4. This means that in this embodiment the second processing means generates a signal indicating eating on lead 10b if the animal is eating. Furthermore the second processing means generates a signal indicating resting on lead 10c if the animal is resting. Also the second processing means generates a signal indicating a rest group on lead 10d if the activity of the animal falls within a rest group. The rest group comprises in this example all activities except for ruminating, eating and resting. Each of these predetermined types of activities can be recognized by means of the second processing means in a well-known manner based on the signals generated by the sensor 4. For this a regular signal processor may be used but also a trained neural network. The sensing of an occurrence of at least one predetermined type of activity of the animal, and in this example, a plurality of predetermined types of activities of the animal respectively, is also referred to as step a. A second sensor such as a switch for detection motions and as indicated by dotted lines may be used for providing further information to the processing means 8 so as to better sensing certain predetermined activities of the animal.

The device further comprises first processing means 12 for determining a length of a time period of a first type during which in step a. a sensed predetermined type of activity has taken place. This means, for example, that if on lead 10a a signal is generated which indicates the occurrence of the activity of the animal being rumination, the first processing means 12 determines how long the rumination takes place. Similarly, if on lead 10b a signal is generated indicating that the animal is eating, the first processing means 12 will determine how long; the eating action continues. The same applies for the activity of resting, from which the occurrence is indicated on lead 10c, and the rest group of activities which is indicated on lead 10d. Thus in a step b. the first processing means determines information about a time period of the first type which corresponds with the duration of the activity ruminating if this predetermined type of activity is detected in step a. Similarly the first processing means also carries out step b. for the other predetermined type of activities which are sensed in step a. This means for example that information about the time period of the first predetermined type is also determined for the activities eating, resting and the rest group respectively. Thus in a step b. it may occur that the first processing means determines information about a time period of the first type which corresponds with the duration of ruminating, eating, resting or the rest group respectively.

In a step c. steps a. and b. are repeated for other sensed predetermined activities. The information which is determined in step b. is transmitted in a step d.

Figure 2A:
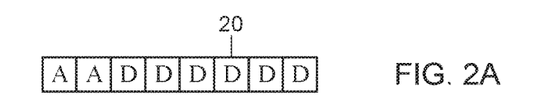
FIG. 2A shows a data format predetermined data block indicating a length of a time period.

The information transmitted in step d is in the format comprising information blocks 20 of a fixed bit length, each information block comprising a first predetermined number of bits indicating which predetermined type of activity has been detected in step a. and a second predetermined number of bits indicating how long the detected predetermined type of activity has taken place wherein the second predetermined number of bits cover a time period which is smaller than a predetermined maximum length in time. FIG. 2A shows such an information block 20. The information block 20 comprises two bits AA for indicating the type of activity and 6 bits DDDDDD for indicating the duration of a sensed activity. The LSB indicated one minute in this example. The MSB indicated 32 minutes in this example. This means that the longest duration which can be indicated by the 6 bits DDDDDD is 63 minutes. This is referred to as the predetermined maximum length in time.

Figure 2B:
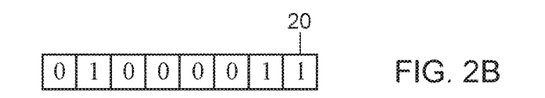
FIG. 2B shows a predetermined data block indicating a length of a time period of a first predetermined type related to rumination.

For example in FIG. 2B the two bits AA have the value 01 which indicated that the first predetermined type of activity (rumination) is sensed. The 6 bits DDDDDD have the value 000011 indicating the duration of the sensed rumination is 3 minutes. In cases the sensed duration of the rumination would be larger than 63 minutes, such as for example 64 minutes, there are two solutions to handle this by means of the data blocks.

Figure 2C:
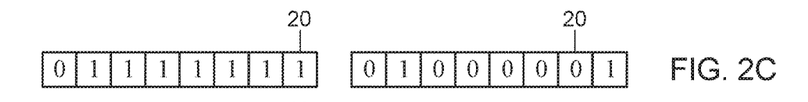
FIG. 2C shows two predetermined data blocks indicating a length of a time period of a first predetermined type related to rumination.

According to a first solution as shown in FIG. 2C the duration of 64 minutes is split into a duration of 63 minutes and a duration of 1 minute. The duration of 63 minutes for, for example, the activity rumination is indicated in the left hand data block as shown in FIG. 2C. The duration of 1 minute for the same rumination is indicated by the right hand data block of FIG. 2C. Thus it holds for example that in case that a length of a time period of the first type is smaller than or equal to the predetermined maximum length in time than the information of a length of a time period of the first type wherein the detected predetermined type of activity has taken place is recorded in one information block wherein in case that a length of a time period of the first type is larger than the predetermined maximum length in time than information of a length of a time period of the first type wherein the detected predetermined type of activity has taken place is recorded in a plurality of information blocks in this example in two data blocks if the duration would be between 64 and 64+63 minutes; three data blocks if the duration would be between 64+63 and 2*64+63 minutes, etc.).

Figure 2D:
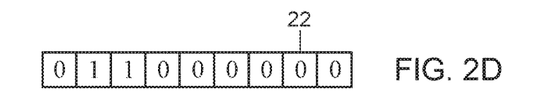
FIG. 2D shows an extended data block indicating a length of a time period of a first predetermined type related to rumination.

According to the second solution, used if the duration would be larger than 63 minutes, the data block will simply be extended with sufficient bits ID to indicate the duration. In this example, wherein the duration is 64 minutes, the data block is extended with one bit D wherein the number 64 is indicated as DDDDDDD=1000000 (see FIG. 2D). Thus in this alternative way it holds that the information of a length of a time period of the first type wherein the detected predetermined type of activity has taken place, is recorded in one extended information block 22 wherein the extended information block comprises a sufficient number of additional bits to store the length of a time period of the first type.

Figure 2E:
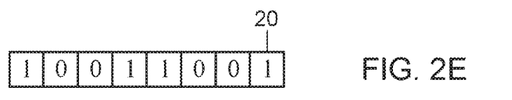
FIG. 2E shows a data block indicating a length of a time period of a first predetermined type related to eating.

For other sensed predetermined activities the duration of these activities is indicated in the same block format as explained above for rumination. For example, the predetermined activity for resting is indicated by AA as 10. Then, if the duration of the activity resting would be 25 minutes, this is indicated by DDDDDD=011001. The obtained data block is shown in FIG. 2E. Again if the duration would be larger than 63 minutes, either a plurality of data blocks would be used in exactly the same manner as discussed for rumination, or an extended data block would be used in exactly the same manner as explained for rumination. In this example the activity eating is indicated by AA=00 and the rest group of activities is indicated by AA=11.

The data blocks are received by means of a receiver 16 and submitted to a central computer 18 for further processing as will be explained hereafter. It is noted that (extended) data blocks may be separated form each other in the receiver 16 by means of well known synchronization applied by the transmitter 14 in the transmitted signals comprising the data blocks. Step d. is repeated on random or predetermined moments in time. Possibly in step d. transmission of a predetermined number of the latest determined information blocks is transmitted. For example in each transmission 96 bytes of information may be transmitted. This means if no extended block can be transmitted (only the block according to FIGS. 2A-2D) that always 96 data blocks are transmitted. Based on experience such a transmission comprises about 17-28 hours of historical information about sensed occurrences associated with the animal.

Figure 3:
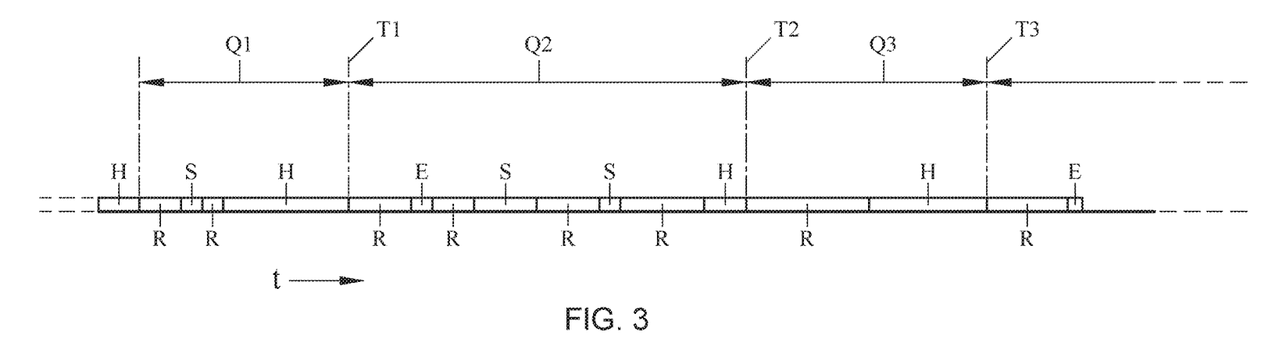
FIG. 3 shows occurrences of different predetermined types of activities as well as schematically determined length of time periods of the first type associated with the predetermined type of activities and determined length of time periods of the second type associated with rumination.

FIG. 3 shows a time line wherein different time periods of the first type are indicated. These time periods can be obtained by the central computer based on the received data blocks 20. A time period having reference number S corresponds with a time period of the first type wherein the animal is resting, a time period with reference character H corresponds with a time period of the first type wherein the animal is ruminating, a time period with reference character E corresponds with a time period of the first type wherein the animal is eating and a time period by the character ill means that a sensed activity occurs, which activity belongs to the rest group.

The central computer 18 is so arranged that it determines, in use, a time period of the second type associated with the predetermined activity rumination. On every moment in time it holds that the time period of the latest second type associated with rumination ends on the moment in time on which the latest time period of the first type associated with the latest sensed occurrence of the ruminating activity ends and which started on the moment in time on which the previous time period of the first predetermined type associated with the activity of rumination has ended. The central computer 18 is so arranged that it determines, in use, a time period of the second type associated the predetermined activity eating. On every moment in time it holds that the time period of the latest second type associated with eating ends on the moment in time on which the latest time period of the first type associated with the latest sensed occurrence of the eating activity ends and which started on the moment in time on which the previous time period of the first predetermined type associated with the activity of eating has ended.

The central computer 18 is so arranged that it determines, in use, a time period of the second type associated the predetermined activity resting. On every moment in time it holds that the time period of the latest second type associated with resting ends on the moment in time on which the latest time period of the first type associated with the latest sensed occurrence of the resting activity ends and which started on the moment in time on which the previous time period of the first predetermined type associated with the activity of resting has ended.

The central computer 18 is so arranged that it determines, in use, a time period of the second type associated the predetermined rest group of activities. On every moment in time it holds that the time period of the latest second type associated with the rest group ends on the moment in time on which the latest time period of the first type associated with the rest group of activities ends and which started on the moment in time on which the previous time period of the first predetermined type associated with the rest group of activities has ended.

Figure 4:
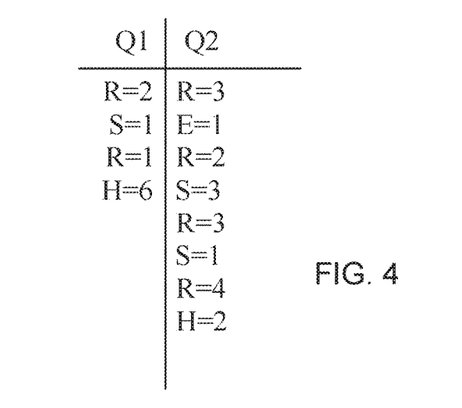
FIG. 4 lists determined lengths of time periods of the first type as shown in FIG. 3 and determined length of time periods of the second type associated with rumination.

In FIG. 4 such time periods of the second type associated with the activity rumination are indicated with the characters Qi (i=1, 2, 3, . . . ). In this example this means that each time period of the second type associated with rumination comprises a time period of the first type which is associated with rumination. For example the time period of the second type which is indicated by Q1, comprises a time period of the first type R which is associated with the rest group, a time period of the first type S which is associated with the occurrence of resting, a time period of the first type R which is associated with the rest group and a time period of the first type H which is associated with rumination.

Similarly the time period of the second type associated with rumination which is indicated with reference Q2, comprises a time period of the first type R which is associated with the rest group, a time period of the predetermined type E which is associated with eating, a time period of the first type B which is associated with the rest group, a time period of the first type S which is associated with resting, a time period of the first type B which is associated with the rest group, a time period of the first type S which is associated with resting, a time period of the first type B which is associated with the rest group and a time period of the first type H which is associated with rumination.

The central computer is further arranged such that, in use, processed information $Y_{f=H}(t)$ about the length of a time period of the first type associated with the predetermined type of activity being ruminating is determined as $Y_{f=H}(t) = at.X_{f=H}(t)+(1-at).Y_{f=H}(t-1)$ wherein $X_{f=H}(t)$ is the length of a time period of the first type associated with the latest sensed predetermined type of activity being rumination divided by the length of the latest determined time period of the second type associated with the predetermined activity of rumination wherein $Y_{f=H}(t-1)$ is the processed information about a previous length of a time period of the first type associated with the first predetermined type of activity being rumination and wherein at is a predetermined factor wherein $0<at\leq1$. It holds in this example that $t=1, 2, 3, \ldots n$. Further it holds that the character f indicated the type of activity. In the above f stands for the predetermined type of activity. In this example f=H.

The central computer is further arranged such that, in use, processed information $Y_{f=E}(t)$ about the length of a time period of the first type associated with the predetermined type of activity being eating is determined as $Y_{f=E}(t)=at.X_{f=E}(t)+(1-at).Y_{f=E}(t-1)$ wherein $X_{f=E}(t)$ is the length of a time period of the first type associated with the latest sensed predetermined type of activity being eating divided by the length of the latest determined time period of the second type associated with the predetermined activity of eating wherein $Y_{f=E}(t-1)$ is the processed information about a previous length of a time period of the first type associated with the first predetermined type of activity of eating and wherein at is a predetermined factor wherein $0<at\leq1$.

The central computer is further arranged such that, in use, processed information $Y_{f=S}(t)$ about the length of a time period of the first type associated with the predetermined type of activity being resting is determined as $Y_{f=S}(t)=at.X_{f=S}(t)+(1-at).Y_{f=S}(t-1)$ wherein $X_{f=S}(t)$ is the length of a time period of the first type associated with the latest sensed predetermined type of activity being resting divided by the length of the latest determined time period of the second type associated with the predetermined activity of resting wherein $Y_{f=S}(t-1)$ is the processed information about a previous length of a time period of the first type associated with the first predetermined type of activity of resting and wherein at is a predetermined factor wherein $0<at\leq1$.

The central computer is further arranged such that, in use, processed information $Y_f(t)$ about the length of a time period of the first type associated with the rest group is determined as $Y_{f=R}(t)=at.X_{f=R}(t)+(1-at).Y_{f=R}(t-1)$ wherein $X_{f=R}(t)$ is the length of a time period of the first type associated with the latest sensed predetermined types of activity associated to the rest group divided by the length of the latest determined time period of the second type associated with the predetermined type of activities associated with the rest group wherein $Y_{f=R}(t-1)$ is the processed information about a previous length of a time period of the first type associated with the rest group wherein at is a predetermined factor wherein $0<at\leq1$. It is noted that if two or more activities of the rest group are directly adjacent to each other on the time line the total duration of this collection of activities forms a predetermined time period of the first type.

It holds in this example that $t=1, 2, 3, \ldots n$. The character f stands for the predetermined type of activity (f=H, R, E or S)

In the above, at may be fixed or it may be equal to the length of the latest time period of the second type divided by a constant factor C. Suppose that the time periods of the first type R, S, H, E in the time periods of the second type Q1 and Q2 have a duration as indicated in FIG. 3 and FIG. 4. Then it follows that Xft for the predetermined type of activity associated with rumination (f=H) which occurred in period Q2 is equal to 2/3+1+2+3+3+1+4+2. The determined processed information $Y_{f=H}(t-n)$ which is determined for the first time in time may for example be set to zero so that $Y_{f=H}(t-n+1)$ (the processed information which is determined for the second time in time) can be determined based on $X_f(t-n+1)$. Thereby, $Y_f(t-n+1)$ can be determined. Than $Y_f(t-n+2)$ can be determined etc. It follows that also $Y_f(t-1)$ can be determined so that also $Y_f(t)$ can be determined with the provided formula based em $Y_f(t-1)$ and $X_f(t)$.

Figure 5:
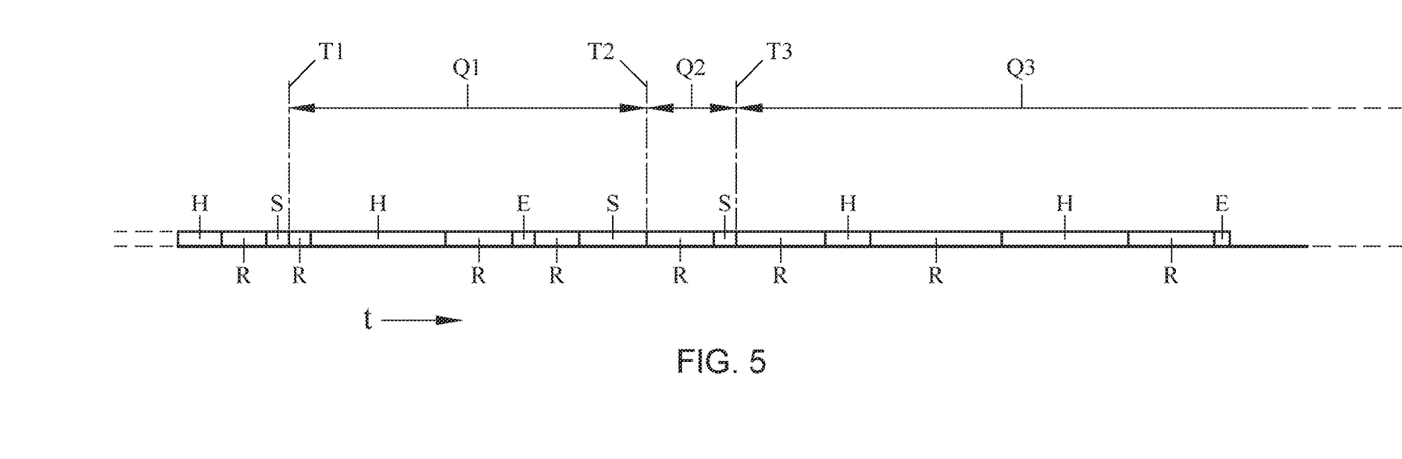
FIG. 5 shows occurrences of different predetermined types of activities as well as schematically determined length of time periods of the first type associated with the predetermined type of activities as shown in FIG. 3 and determined length of time periods of the second type associated with resting.
Figure 6:
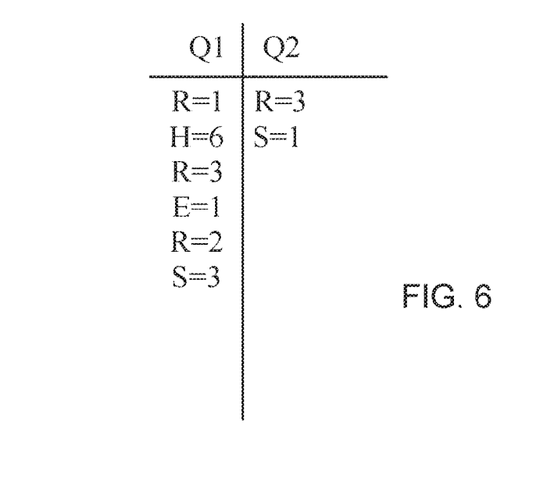
FIG. 6 lists determined lengths of time periods of the first type as shown in FIG. 5 and determined length of time periods of the second type associated with resting.

In FIGS. 5 and 6 for the same sequence of events as indicated in FIG. 2 the time periods of the second type associated with resting (S) are indicated.

If the other activity is, for example, resting (f=S), then $X_{f=S}(t)$ associated with resting is determined as 3/6+3+1+2+3. Similarly as discussed above, $Y_{f=S}(t-n)$ associated with the activity of resting which is determined for the first time in time can be set to zero so that $Y_{f=S}(t-n+1)$ can be determined based on $X_{f=S}(t-n+1)$ associated with resting. This also means that $Y_{f=S}(t-1)$ associated with resting can be determined so that also $Y_{f=S}(t)$ associated with resting can be determined with the provided formula based on $Y_{f=S}(t-1)$ and $X_{f=S}(t)$.

In the above at is fixed or at is the length of the time period of the latest determined time period of the second type divided by a constant factor C. The constant factor C may be the length of a predetermined time interval such as one day. It will now be clear that $X_{f=R}(t)$ and $X_{f=E}(t)$ can be determined in the same way as discussed above for $X_{f=H}(t)$ and $X_{f=S}(t)$.

The first processing means may comprise a regular microprocessor or a neural network. It is also possible that the first and second processing means are the same processing means and are formed by a microprocessor.

The invention claimed is:

1. A method of monitoring the physiological condition of ruminant animals, or monitoring suitability of animal feed for ruminant animals, the method comprising:
   a. sensing the occurrence of at least one predetermined type of activity of the animal;
   b. determining information about a time period of the first type which corresponds with the duration of the at least one predetermined type of activity which is detected in step a.;
   c. repeating steps a. and b. for a next sensed occurrence of activities of the at least one predetermined type;

d. transmitting the information determined in steps b.; characterized in that, the information transmitted in step d is in the format of information blocks of a fixed bit length, each information block comprising a first predetermined number of bits indicating which predetermined type of activity has been detected in step a. and a second predetermined number of bits indicating the information about a time period of the first type as determined in step b. and associated with the sensed occurrence in step a. wherein the second predetermined number of bits cover a time period which is smaller than or equal to a predetermined maximum length in time, wherein the method comprises further a step e. wherein the information transmitted in step d. is received and a step f. wherein based on the received information in a step e. a time period of the second type associated with the at least one predetermined activity is determined which ends on the moment in time on which the time period of the first type associated with the latest sensed occurrence of the at least one predetermined type of activity has ended and which starts on the moment in time on which the previous time period of the first type associated with the previous sensed occurrence of the at least one predetermined type of activity has ended and wherein the method comprises further a step g. wherein based on the received information in step f. processed information Yf(t) about the length of a time period of the first type associated with the at least one predetermined type of activity is determined as $Yf(t)=at \cdot Xf(t)+(1-at) \cdot Yf(t-1)$ wherein Xf(t) is the length of a time period of the first type associated with the latest sensed at least one predetermined type of activity (f) divided by the length of the latest determined time period of the second type associated with the at least one predetermined type of activity (1) wherein Yf(t-1) is the processed information about a previous determined length of a time period of the first type associated with the at least one predetermined type of activity (f) and wherein at is a predetermined factor wherein $0 < at \le 1$ and wherein f stands for the at least one predetermined type of activity.

2. The method according to claim 1 wherein in case that a length of a time period of the first type is smaller than or equal to the predetermined maximum length in time than the information of a determined length of a time period of the first type wherein the associated detected predetermined type of activity has taken place is recorded in one information block wherein in case that a length of a time period of the first type is larger than the predetermined maximum length in time than: the information of a length of a time period of the first type wherein the associated detected predetermined type of activity has taken place is recorded in a plurality of information blocks or the information of a length of a time period of the first type wherein the associated detected predetermined type of activity has taken place, is recorded in one extended information block wherein the extended information block comprises a sufficient number of additional bits to store the information about the length of a time period of the first type.

3. The method according to claim 1 wherein step a. and step b. are carried out for a plurality of predetermined type of activities respectively.

4. The method according to claim 1 wherein in step d. transmission is repeated on random or predetermined moments in time.

5. The method according to claim 4 wherein in step d. a predetermined number of the latest determined information blocks is transmitted.

6. The method according to claim 1 wherein at is fixed or at is the length of the latest determined time period of the second type divided by a constant factor C.

7. The method according to claim 6 wherein the constant factor C is the length of a predetermined time interval such as one day.

8. The method according to claim 1 wherein the at least one predetermined type of activity (f) is ruminating (f=H), eating (f=E) or resting (f=S).

9. The method according to claim 8 wherein the method is carried out for each sensed activity in step a which is ruminating, eating or resting.

10. The method according to claim 1 wherein the method is carried out by means of a system comprising at least one sensor for carrying out at least a part of step a., a first processing means for carrying out at least a part of step b. and transmitter for carrying out at least step d.

11. The method according to claim 10 wherein in step a. movements of the animal are detected by means of the at least one sensor and the occurrence of the at least one predetermined type of activity of the animal is detected based on the detected movements by means of a second processing means.

12. The method according to claim 11 wherein the second processing means comprises a neural network or a microprocessor.

13. The method according to claim 11 wherein the first and second processing means are combined into one processing means.

14. The method according to claim 10 wherein a tag is attached to the animal and wherein the tag comprises the sensor, the first processing means, and the transmitter.

15. A system for monitoring the physiological condition of ruminant animals, or suitability of animal feed for ruminant animals, the system comprising at least one sensor for carrying out at least a part of a step a., a first processing means arranged for carrying out at least a part of a step b., a transmitter for carrying out at least a step d. and wherein the system is arranged for repeating in a step c. steps a. and, b. for a next sensed occurrence of activities of the at least one predetermined type, wherein step a. comprises sensing the occurrence of the at least one predetermined type of activity of the animal, step b comprises determining by means of the first processing means information about a time period of the first type which corresponds with the duration of the at least one predetermined type of activity which is detected in step a., step d. comprises transmitting the information determined in steps b., wherein, the information transmitted in step d. is in the format of information blocks of a fixed bit length, each information block comprising a first predetermined number of bits indicating which predetermined type of activity has been detected in step a. and a second predetermined number of bits indicating the information about a time period of the first type as determined in step b. and associated with the sensed occurrence in step a. wherein the second predetermined number of bits cover a time period which is smaller than or equal to a predetermined maximum length in time, wherein the system is further provided with a receiver and a central computer communicatively connected with the receiver wherein the system is also arranged such that, in use, a step e. and a step f. are carried out wherein in step e. by means of the receiver the information transmitted in step d. is received and wherein in step f. based on the received information in a step e. by means of the central computer a time period of the second type associated with the at least one predetermined type of activity is determined which ends on the moment in time on which the time period of the first type associated with the latest sensed occurrence of the at least one predetermined type of activity has ended and which starts on the moment in time on which the previous time period of the first type associated with the previous sensed occurrence of the at least one predetermined type of activity has ended and wherein the system is also arranged such that, in use, further a. step g. is carried out by means of the central computer, wherein based on the received information in step g. processed information Yf(t) about the length of a time period of the first type associated with the at least one predetermined type of activity (f) is determined as $Yf(t)=at \cdot Xf(t)+(1-at) \cdot Yf(t-1)$ wherein Xf(t) is the length of a time period of the first type associated with the latest sensed at least one predetermined type of activity (f) divided by the length of the latest determined time period of the second type associated with the at least one predetermined type of activity (f) wherein Yf(t−1) is the process information about previous determined information about a length of a time period of the first type associated with the at least one predetermined type of activity (f) and wherein at is a predetermined factor wherein $0 < at \leq 1$ and wherein f stands for the at least one predetermined type of activity.

16. The system according to claim 15 wherein the system is also arranged such that, in use, that in case that a length of a time period of the first type is smaller than or equal to the predetermined maximum length in time than the information of a determined length of a time period of the first type wherein the associated detected predetermined type of activity has taken place is recorded in one information block wherein, in case that a length of a time period of the first type is larger than the predetermined maximum length in time than: the information of a length of a time period of the first type wherein the associated detected predetermined type of activity has taken place is recorded in a plurality of information blocks or the information of a length of a time period of the first type wherein the associated detected predetermined type of activity has taken place is recorded in one extended information block wherein the extended information block comprises a sufficient number of additional bits to store the information about the length of a time period of the first type.

17. The system according to claim 15 wherein the system is also arranged such that, in use, step a. and step b. are carried for a plurality of predetermined type of activities respectively.

18. The system according to claim 15 wherein the system is also arranged such that, in use, in step d. transmission is repeated on random or predetermined moments in time.

19. The system according to claim 18 wherein the system is also arranged such that, in use, in step d. transmission of a predetermined number of the latest determined information blocks is transmitted.

20. The system according to claim 15 wherein the system is also arranged such that, in use, at is fixed or at is the length of the latest determined time period of the second type divided by a constant factor C.

21. The system according to claim 20 wherein the system is also arranged such that, in use, the constant factor C is the length of a predetermined time interval such as one day.

22. The system according to claim 15 wherein the system is also arranged such that, in use, the at least one predetermined type of activity (f) is ruminating (f=H), eating (f=E) or resting (f=S).

23. The system according to claim 22 wherein the system is also arranged such that, in use, the steps are also carried out for each sensed activity in step a. which is ruminating, eating or resting respectively.

24. The system according to claim 15 wherein the system is further provided with second processing means which is arranged such that, in use, in step a. movements of the animal are detected by means of the at least one sensor and the occurrence of the at least one predetermined type of activity of the animal is detected based on the detected movements by means of the second processing means.

25. The system according to claim 23 wherein the second processing means comprises a neural network or a microprocessor.

26. The system according to claim 24 wherein the first and second processing means are combined into one processing means.

27. The method according to claim 9, wherein the method is carried out for each sensed activity in step a which is for a rest group of activities (f=R) which differ from ruminating, resting and eating.

28. The method according to claim 14, wherein the tag further comprises a second processing means.

29. The system according to claim 23, wherein the system is also arranged such that, in use, the steps are also carried out for each sensed activity in step a. which is for a rest group of activities (f=R) which differ from rumination, resting and eating.

* * * * *